United States Patent
Guo et al.

(10) Patent No.: US 11,202,600 B2
(45) Date of Patent: Dec. 21, 2021

(54) MULTIFUNCTIONAL NEUROPHYSIOLOGIC MONITORING AND PROBING SYSTEM AND A METHOD OF IMPLEMENTING THE SAME

(71) Applicants: Qiang Guo, Guangdong (CN); Zhengwei Guo, Guangdong (CN); Junying Feng, Guangdong (CN)

(72) Inventors: Qiang Guo, Guangdong (CN); Zhengwei Guo, Guangdong (CN); Junying Feng, Guangdong (CN)

(*) Notice: Subject to any disclaimer, the term of this patent is extended or adjusted under 35 U.S.C. 154(b) by 681 days.

(21) Appl. No.: 16/088,449

(22) PCT Filed: Sep. 4, 2017

(86) PCT No.: PCT/CN2017/100338
§ 371 (c)(1),
(2) Date: Sep. 26, 2018

(87) PCT Pub. No.: WO2019/037154
PCT Pub. Date: Feb. 28, 2019

(65) Prior Publication Data
US 2021/0267533 A1    Sep. 2, 2021

(30) Foreign Application Priority Data
Aug. 24, 2017   (CN) .................. 201710735754.5

(51) Int. Cl.
*A61B 5/00* (2006.01)

(52) U.S. Cl.
CPC .......... *A61B 5/4041* (2013.01); *A61B 5/4836* (2013.01); *A61B 5/4893* (2013.01); *A61B 5/746* (2013.01); *A61B 2560/04* (2013.01)

(58) Field of Classification Search
CPC ....... A61B 5/4893; A61B 5/4041; A61B 5/40; A61B 5/4076; A61B 6/506
See application file for complete search history.

(56) References Cited

U.S. PATENT DOCUMENTS

| | | | |
|---|---|---|---|
| 6,306,100 B1 * | 10/2001 | Prass ...................... | A61B 5/389 600/554 |
| 2009/0177112 A1 * | 7/2009 | Gharib ................. | A61B 5/4893 600/554 |

* cited by examiner

*Primary Examiner* — Eric F Winakur

(57) ABSTRACT

A multifunctional neurophysiologic monitoring and probing system, having a main unit (1), a main wire (2), negative electrode neurophysiologic monitoring and probing parts and positive electrode neurophysiologic monitoring and probing parts; one end of the main wire (2) is connected with the main unit (1); another end of the main wire is divided into two branch wires connecting with the negative electrode neurophysiologic monitoring and probing parts and the positive electrode neurophysiologic monitoring and probing parts respectively.

9 Claims, 1 Drawing Sheet

MULTIFUNCTIONAL NEUROPHYSIOLOGIC MONITORING AND PROBING SYSTEM AND A METHOD OF IMPLEMENTING THE SAME

BACKGROUND OF THE INVENTION

The present invention relates to the technical field of neurophysiologic monitoring, and more specifically relates to a multifunctional neurophysiologic monitoring and probing system and a method of implementing the same.

A patient may suffer from neurophysiologic damage due to factors such as preoperative injury or surgery, resulting in corresponding functional deterioration. However, the growth rate of an injured nerve is as slow as about 1 mm/day, and 1% of nerve function will be lost every 6 days of delayed treatment. Treatment time is very critical to functional recovery after peripheral nerve injury. Early diagnosis helps the preparation of customized treatment plan and favors the timing of operation so as to maximize functional recovery of a nerve. Factors like fracture, traction, compression, and amputation of limbs can often cause peripheral nerve injury of a patient. Neurophysiologic damage during surgery is more common where surgeons are not familiar with neuroanatomy, in patents with neuroanatomical variation, and clamping, cutting, unreasonable ligation or excessive pulling of nerves. Thyroid surgery is a common type of surgery. During operation, recurrent laryngeal nerve injury is caused by clamping, cutting, unreasonable ligation or excessive pulling of the nerve. Unilateral recurrent laryngeal nerve injury can cause hoarseness, and bilateral recurrent laryngeal nerve injury can result in dyspnea and even suffocation that may lead to death; modified radical mastectomy is the main surgical treatment of breast cancer, such treatment method ensures curative effect, while minimizing the local aesthetic and functional damage caused by the surgery, however, corresponding nerves may be damaged by the surgical operation, causing functional deterioration of thoracodorsal nerve innervation latissimus dorsi, thoracic nerve innervation pectoral muscle, and chest long nerve innervation serratus. In particular, chest nerve injury can cause atrophy of retained pectoralis major muscle after surgery, and in turns result in deformation of chest and arms that causes functional deterioration of the upper limbs of the affected body portion of the patient; in limb surgery and spinal treatment, bone fractures, hematoma compression, and iatrogenic injury can cause neurophysiologic damage; face surgery such as parotid gland can cause facial nerve injury. In order to effectively reduce neurophysiologic damage during surgery, common clinical measures include the following: (1) current methods for preoperative diagnosis of peripheral nerve injury include clinical checking and electromyograms, etc., but it is difficult to achieve completely accurate diagnosis, especially in cases where a patient shows no sign of functional recovery as a clinical result but is found to have neurological continuity during surgery; therefore, it is difficult for a surgeon to determine the functional status of a nerve. Accordingly, protection of remaining normal nerves and existing regenerated nerves in peripheral nerve surgery is an important issue. However, in current surgical operations, it is limited by naked eye observation and palpation to determine whether the peripheral nerve function is defective or not. (2) Although a surgeon may be familiar with neuroanatomy due to accumulation of practicing time and experience, neurologic injury of patents with neuroanatomical variation may not be avoided during surgery, and neurologic functional injury that has been caused may not be discovered in an early stage. (3) Conventional method of separating exposed nerves during surgery is to identify the nerve by naked eyes and separate the exposed nerve by nerve stripper. This not only increases the operation time, but also fails to avoid neurologic damage of patients with neuroanatomical variation. Also, the use of naked eyes can only guarantee visual integrity of the nerves. Non-disruptive injuries caused by traction, heat conduction, and suture cutting can by no means detected by naked eyes, and neurologic functional injury that has been caused may not be discovered in an early stage. (4) In neurophysiological monitoring using electricity, preoperative electromyography of peripheral nerves has a higher probability of obtaining false positive and false negative results, and this results in difficult decision making in continuous neurological surgery. Intraoperative neurophysiologic monitoring (IONM) mechanism observes the function of the nerves by transforming the activity of the muscles into myoelectric signal. IONM can assist the surgeon to identify the nerves and blood vessels in order to quickly determine routing of the nerves, reduce the lengths of free nerves, ensure the integrity of the neurophysiologic function to a maximal extent, and reduce neurophysiologic damage. IONM favors discovery of neurophysiologic damage factors and timely repair of the damaged nerves during surgery. The accuracy of intraoperative electrophysiological detection for peripheral nerve surgery is better than preoperative electromyography in terms of accuracy, simplicity and its real-time nature that may directly assist in selection of intraoperative surgical plan. In neurophysiologic compression injury caused by nerve lumps etc, intraoperative electrophysiological detection can evaluate the curative effect and determine the prognosis.

Traditional electrophysiological diagnosis has positive significance for definite diagnosis, evaluation of the prognosis of recovery after neurophysiologic injury, and staging of peripheral entrapment neuropathy. However, electrophysiological examination has its own limitations: physiological monitoring apparatus are expensive, and require professional operators. In peripheral neurological surgery, preoperative electromyography of peripheral nerves has a higher probability of obtaining false positive and false negative results, and this results in difficult decision making in continuous neurological surgery, thereby not being suitable for use by this type of surgery, in addition, due to factors like technical error in actual operation process, anatomical variations and other physiological factors, the results of electrophysiological diagnosis may contradict with clinical examination results. Intraoperative neurologic monitoring (IONM) requires a helper to separate exposed tissue in neurological probing of deep tissue, and a specialized operator is required for neurophysiologic monitoring. Therefore, neurophysiologic monitoring and probing cannot be performed by a single person, and there are limitations for neurophysiologic probing of back nerves of deep tissues.

Neurostimulators are widely used for nerve locating in peripheral nerve blocking. However, neurostimulators only perform neurophysiologic probing, and cannot simultaneously achieve stripping and exposing of nerves and determining the routing of the nerves.

BRIEF SUMMARY OF THE INVENTION

In view of the aforesaid disadvantages now present in the prior art, the present invention provides a multifunctional neurophysiologic monitoring and probing system which is simple and safe, and can effectively probe the nerves, locate the nerves and a routing thereof accurately, strip and expose the nerves, shortens surgery time, timely discover neurophysiologic injury, and avoid morphological and functional injury of the nerves.

Another object of the present invention is to provide a method of implementing the multifunctional neurophysiologic monitoring and probing system.

The technical solution of the present invention is detailed as follows:

A multifunctional neurophysiologic monitoring and probing system, comprising a main unit, a main wire, negative electrode neurophysiologic monitoring and probing parts and positive electrode neurophysiologic monitoring and probing parts; wherein one end of the main wire is connected with the main unit; another end of the main wire is divided into two branch wires connecting with the negative electrode neurophysiologic monitoring and probing parts and the positive electrode neurophysiologic monitoring and probing parts respectively.

The negative electrode neurophysiologic monitoring and probing parts comprise a negative electrode branch wire being one of the two branch wires, a negative electrode branch wire insertion end, a negative electrode nerve probe connecting opening, a negative electrode nerve probe, a negative electrode nerve probe switch, a negative electrode nerve probe insulator, a negative electrode nerve probe front end conductor, and a negative electrode nerve probe conductor; wherein one end of the negative electrode branch wire is connected with the main wire; another end of the negative electrode branch wire is connected with the negative electrode branch wire insertion end; the negative electrode nerve probe connecting opening is provided on the negative electrode nerve probe; the negative electrode nerve probe connecting opening is connected with the negative electrode branch wire insertion end; the negative electrode nerve probe switch, the negative electrode nerve probe insulator, the negative electrode nerve probe front end conductor, and the negative electrode nerve probe conductor are all provided on the negative electrode nerve probe; the negative electrode nerve probe switch is a switch for turning on and off a stimulating current; the negative electrode nerve probe insulator wraps the negative electrode nerve probe conductor; the negative electrode nerve probe front end conductor is provided at a top end of the negative electrode nerve probe conductor and protrudes out of the negative electrode nerve probe insulator.

The positive electrode neurophysiologic monitoring and probing parts comprise a positive electrode branch wire being another one of the two branch wires, a positive electrode branch wire switch, a peripheral electrode, a positive electrode branch wire insertion end, a positive electrode nerve probe connecting opening, a positive electrode nerve probe, a positive electrode nerve probe insulator and a positive electrode nerve probe conductor; wherein one end of the positive electrode branch wire is connected with the main wire; another end of the positive electrode branch wire is connected with both the peripheral electrode and the positive electrode branch wire insertion end via the positive electrode branch wire switch; the positive electrode nerve probe connecting opening is provided on the positive electrode nerve probe; and the positive electrode nerve probe connecting opening is connected with the positive electrode branch wire insertion end; the positive electrode nerve probe insulator and the positive electrode nerve probe conductor are both provided on the positive electrode nerve probe; the positive electrode nerve probe insulator wraps the positive electrode nerve probe conductor.

The main unit controls an intensity and frequency of electrical stimulation being output, and the main unit also shows electroneurography and alert signals, and also plays audio signals.

Preferably, the negative electrode nerve probe connecting opening is removable from the negative electrode branch wire for replacement of other different negative electrode nerve probes of different types and functions.

Preferably, the positive electrode nerve probe connecting opening is removable from the positive electrode branch wire for replacement of other different positive electrode nerve probes of different types and functions.

Preferably, the negative electrode nerve probe is shapable into an arc shape or a hook shape.

Preferably, the positive electrode nerve probe is shapable into an arc shape or a hook shape.

Preferably, the negative electrode nerve probe insulator of the negative electrode nerve probe does not completely wrap the negative electrode nerve probe conductor, wherein one side of the negative electrode nerve probe is insulated, and another side of the negative electrode nerve probe is electrically conductive.

Preferably, the positive electrode nerve probe insulator of the positive electrode nerve probe does not completely wrap the positive electrode nerve probe conductor, wherein one side of the positive electrode nerve probe is insulated, and another side of the positive electrode nerve probe is electrically conductive.

A method of implementing the multifunctional neurophysiologic monitoring and probing system, comprising the following steps:

(1) before surgery starts, sterilizing a patient according to routine procedures, attaching the peripheral electrode to an affected side of the patient, and placing a surgical towel; connecting one end of the main wire to the main unit positioned under an operation table, and connecting another end of the main wire with the positive electrode branch wire, and then connecting the positive electrode branch wire with the peripheral electrode via the positive electrode branch wire switch;

(2) at the beginning of the surgery, when probing an unimportant nerve distribution area, selecting the positive electrode nerve probe for separating and exposing tissues, or separating the positive electrode nerve probe from the positive electrode branch wire insertion end, and directly using the positive electrode nerve probe alone for separating and exposing the tissues; according to practical needs of the surgery, processing the negative electrode nerve probe in the same way as the positive electrode nerve probe;

(3) during the surgery, when probing an important nerve distribution area or an uncertain area, turning on the main unit, setting an intensity and frequency of the electrical stimulation being output; when probing for a motor nerve in a tissue region, performing the probing by unipolar nerve stimulation, which comprises switching the positive electrode branch wire switch to the peripheral electrode, and turning on the negative electrode nerve probe switch to form a unipolar nerve stimulation path using the negative electrode nerve probe and the peripheral electrode, and performing the unipolar nerve stimulation via the negative electrode nerve probe front end conductor; alternatively, shaping a front end of the negative electrode nerve probe into a curved shape or a hook shape to perform probing, separating and exposing nerves in tissues of different body parts; after probing, determining whether the tissue contains any motor or mixed nerve distribution, and then carrying out a corresponding surgical treatment; when there are muscle reactions due to response of the nerve to the electrical stimulation, reducing the intensity of the electrical stimulation from large to small, to preliminarily determine a distance between the nerve and a corresponding electrode stimuli; when probing for a routing of the motor nerve in the tissue region, performing the probing by bipolar nerve stimulation, which comprises switching the positive electrode branch wire switch to the positive electrode nerve probe, and turning on the negative electrode nerve probe switch to form a bipolar nerve stimulation path using the negative electrode nerve probe and the positive electrode nerve probe, and performing the bipolar nerve stimulation to probe the motor or mixed nerve to discover nerve distribution and routing; after probing, determining whether the tissue contain any motor or mixed nerve distribution, and then carrying out a corresponding surgical treatment to prevent the surgery from damaging the nerve; wherein, when the tissue is found to contain motor or mixed nerve distribution after probing, continuing to separate and expose the nerve of the tissue by using the unipolar nerve stimulation or the bipolar nerve stimulation, so as not to damage the nerve during surgery; when there is no corresponding muscle reaction or electrophysiological sign in response to the electrical stimulation of a corresponding nerve distribution area, confirming a corresponding damage of nerve function, and then timely performing probing and repair treatment of the damaged nerve, thereby improving safety and quality of the surgery.

(4) after major operation is completed during the surgery, determining whether peripheral nerve is functionally damaged using the unipolar nerve stimulation or the bipolar nerve stimulation and/or intraoperative electrophysiological examination, and if yes, timely performing probing and repair of damaged peripheral nerve, thereby improving safety and quality of the operation.

Preferably, according to operation requirements of different surgical sites, disconnecting the positive electrode nerve probe or the negative electrode nerve probe from their corresponding insertion ends, and replacing the positive electrode nerve probe or the negative electrode nerve probe with another positive electrode nerve probe or another negative electrode nerve probe of different types and functions respectively.

An operating principle of the present invention is detailed as follows:

Before surgery, sterilizing a patient according to routine procedures, attaching the peripheral electrode to an affected side of the patient and placing a surgical towel; connecting one end of the main wire to the main unit positioned under an operation table, connecting another end of the main wire to the positive electrode branch wire; connecting the positive electrode branch wire with the peripheral electrode via the positive electrode branch wire switch; the surgery is now started, and when probing an unimportant nerve distribution area, selecting the positive electrode nerve probe for separating and exposing tissues, or separating the positive electrode nerve probe from the positive electrode branch wire electrode insertion end, and directly using the positive electrode nerve probe alone for separating and exposing the tissues; according to the practical needs of the surgery, the negative electrode nerve probe can also be operated according to the operation of the positive electrode nerve probe; during surgery, when probing an important nerve distribution area or an uncertain area, turning on the main unit, setting the intensity and frequency of the electrical stimulation being output; if probing for a motor nerve in a tissue region, the probing is carried out by unipolar nerve stimulation, specifically, switching the positive electrode branch wire switch to the peripheral electrode, and turning on the negative electrode nerve probe switch, so that the negative electrode nerve probe and the peripheral electrode form a unipolar nerve stimulation path, and the unipolar nerve stimulation is performed by the negative electrode nerve probe front end conductor, or a front end of the negative electrode nerve probe is shaped into a curved shape or a hook shape to perform probing, separating and exposing nerves in tissues of different body parts; after probing, it can be determined whether the tissue contain any motor nerve or mixed nerve distribution, and then a corresponding surgical treatment can follow; if there are muscle reactions due to response of a nerve to electrical stimulation, the intensity of the electrical stimulation is adjusted from large to small to preliminarily determine a distance between the nerve and the electrode stimuli; if probing for a routing of the motor nerve in the tissue region, probing is carried out by bipolar nerve stimulation, specifically, switching the positive electrode branch wire switch to the positive electrode nerve probe, and turning on the negative electrode nerve probe switch, and the negative electrode nerve probe and the positive electrode nerve probe form a bipolar stimulation path, and the bipolar nerve stimulation is used to probe motor or mixed nerve to discover nerve distribution and routing; after probing, it is known whether the tissue contains any motor or mixed nerve distribution, and then a corresponding surgical treatment will be carried out, so as not to damage the nerve during surgery; if after probing, the tissue is found to contain motor or mixed nerve distribution, continue to separate and expose the nerve of the tissue with the help of unipolar or bipolar nerve stimulation, so as not to damage the nerve during surgery; if there is no corresponding muscle reaction or electrophysiological sign in response to the electrical stimulation of the corresponding nerve distribution area, it is determined that the corresponding nerve function is damaged, and then probing and repair treatment of the damaged nerve can be performed timely, thereby improving the safety and quality of the surgery; according to operation requirements of different surgical sites, the positive electrode nerve probe or the negative electrode nerve probe may be disconnected from their respective insertion ends, and being replaced with another positive electrode nerve probe or negative electrode nerve probe of different types, sizes, and functions; after main operation is completed during surgery, unipolar or bipolar nerve electrical stimulation and intraoperative electrophysiological examination can be used to determine whether peripheral nerve function is damaged; if the peripheral nerve is functionally injured, timely probing and repair can be carried out, thereby improving the safety and quality of the operation.

Compared with the prior arts, the present invention has the following beneficial effects:

(1) The present invention can monitor the intraoperative electrophysiological status in real time during surgery, and can also observe movements of muscles innervated by corresponding motor or mixed nerves by unipolar or bipolar electrical stimulation, to locate the positions and routing of the nerves, thereby simply, safely and effectively probe the nerves and complete nerve probing and exposure of free nerves, also the present invention timely detects the integrity of neurologic functions, shortens the operation time, avoids damage to the nerves and timely detects morphological and functional injury of the nerves.

(2) The positive electrode nerve probe and the negative electrode nerve probe of the present invention are dismountable and replaceable with other types and models of probes to target probing, separating and exposing nerves of the tissues of different body parts; the front end conductors of the probes are slightly protruded from the corresponding insulators, and can be shaped into a curved shape or a hook shape etc, to perform probing, separating and exposing nerves in tissues of different body parts, and it is particularly advantageous for neurophysiologic monitoring and probing and tissue separation in deep tissue and the back thereof. As such, the present invention fully exposes nerves, shortens operation time, reduces intraoperative bleeding and nerve damages.

One side of each of the positive and negative nerve probes is insulated, and another side is electrically conductive, and this configuration can reduce erroneous determination due to the impact of electrical stimulation on the nerves of non-targeted tissues, accordingly, errors can be reduced.

Reference signs in the figures: 1—main unit; 2—main wire; 3—negative electrode branch wire; 4—negative electrode branch wire insertion end; 5—negative electrode nerve probe connecting opening; 6—negative electrode nerve probe switch; 7—negative electrode nerve probe insulator; 8—negative electrode nerve probe front end conductor; 9—negative electrode nerve probe conductor; 10—negative electrode nerve probe; 11—positive electrode branch wire; 12—positive electrode branch wire switch; 13—peripheral electrode; 14—positive electrode branch wire insertion end; 15—positive electrode nerve probe connecting opening; 16—positive electrode nerve probe; 17—positive electrode nerve probe conductor; 18—positive electrode nerve probe insulator.

DETAILED DESCRIPTION OF THE INVENTION

The present invention will be described further in detail below with reference to an embodiment and the accompanying drawings. However, the present invention should not be limited to the embodiment disclosed herein.

Figure 1:
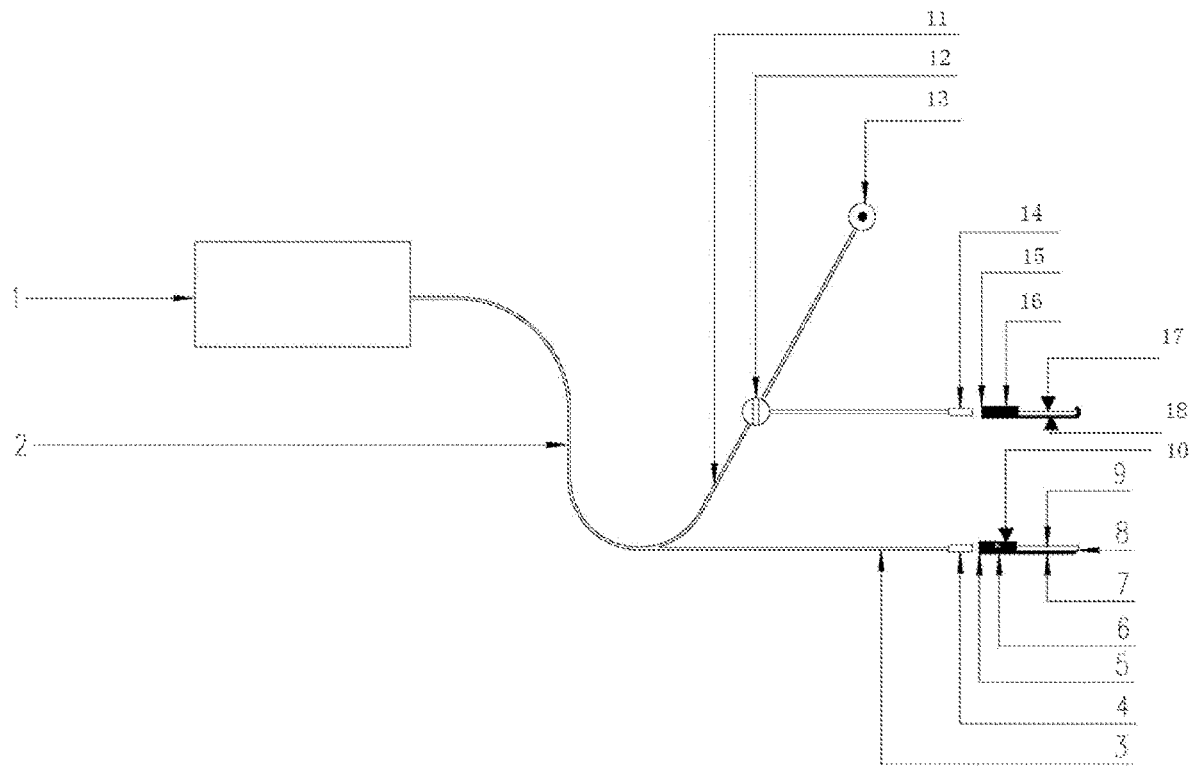
FIG. 1 is a schematic structural view of the present invention.
Figure 2:
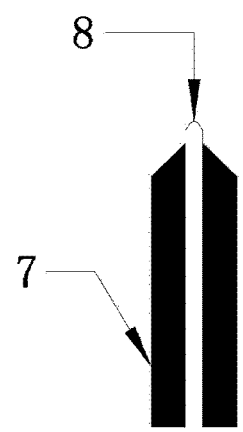
FIG. 2 is a schematic structural view of a negative electrode nerve probe.

As shown in FIGS. 1-2, a multifunctional neurophysiologic monitoring and probing system, comprising a main unit 1, a main wire 2, negative electrode neurophysiologic monitoring and probing parts and positive electrode neurophysiologic monitoring and probing parts; one end of the main wire 2 is connected with the main unit 1; another end of the main wire 2 is divided into two branch wires connecting with the negative electrode neurophysiologic monitoring and probing parts and the positive electrode neurophysiologic monitoring and probing parts respectively.

The negative electrode neurophysiologic monitoring and probing parts comprise a negative electrode branch wire 3, a negative electrode branch wire insertion end 4, a negative electrode nerve probe connecting opening 5, a negative electrode nerve probe 10, a negative electrode nerve probe switch 6, a negative electrode nerve probe insulator 7, a negative electrode nerve probe front end conductor 8, and a negative electrode nerve probe conductor 9, wherein one end of the negative electrode branch wire 3 is connected with the main wire 2; another end of the negative electrode branch wire 3 is connected with the negative electrode branch wire insertion end 4; the negative electrode nerve probe connecting opening 5 is provided on the negative electrode nerve probe 10; the negative electrode nerve probe connecting opening 5 is connected with the negative electrode branch wire insertion end 4; the negative electrode nerve probe connecting opening 5 is removable from the negative electrode branch wire 3 for replacement of different negative electrode nerve probes of different types and functions; the negative electrode nerve probe switch 6, the negative electrode nerve probe insulator 7, the negative electrode nerve probe front end conductor 8, and the negative electrode nerve probe conductor 9 are all provided on the negative electrode nerve probe 10; the negative electrode nerve probe switch 6 is a switch for turning on and off a stimulating current; the negative electrode nerve probe insulator 7 wraps the negative electrode nerve probe conductor 9; specifically, the negative electrode nerve probe insulator 7 of the negative electrode nerve probe 10 does not completely wrap the negative electrode nerve probe conductor 9; in other words, one side of the negative electrode nerve probe 10 is insulated, while another side of the negative electrode nerve probe 10 is electrically conductive. The negative electrode nerve probe front end conductor 8 is provided at a top end of the negative electrode nerve probe conductor 9 and protrudes out of the negative electrode nerve probe insulator 7; the negative electrode nerve probe 10 is shapable into for example an arc shape or a hook shape.

The positive electrode neurophysiologic monitoring and probing parts comprise a positive electrode branch wire 11, a positive electrode branch wire switch 12, a peripheral electrode 13, a positive electrode branch wire insertion end 14, a positive electrode nerve probe connecting opening 15, a positive electrode nerve probe 16, a positive electrode nerve probe insulator 18 and a positive electrode nerve probe conductor 17; one end of the positive electrode branch wire 11 is connected with the main wire 2; another end of the positive electrode branch wire 11 is connected with both the peripheral electrode 13 and the positive electrode branch wire insertion end 14 via the positive electrode branch wire switch 12; the positive electrode nerve probe connecting opening 15 is provided on the positive electrode nerve probe 16; and the positive electrode nerve probe connecting opening 15 is connected with the positive electrode branch wire insertion end 14; the positive electrode nerve probe connecting opening 15 is removable from the positive electrode branch wire 11 for replacement of different positive electrode nerve probes of different types and functions; the positive electrode nerve probe insulator 18 and the positive electrode nerve probe conductor 17 are both provided on the positive electrode nerve probe 16; the positive electrode nerve probe insulator 18 wraps the positive electrode nerve probe conductor 17; specifically, the positive electrode nerve probe insulator 18 of the positive electrode nerve probe 16 does not completely wrap the positive electrode nerve probe conductor 17; in other words, one side of the positive electrode nerve probe 16 is insulated, and another side of the positive electrode nerve probe 16 is electrically conductive; the positive electrode nerve probe 16 is shapable into for example an arc shape or a hook shape.

The main unit 1 controls the intensity and frequency of output electrical stimulation, and the main unit 1 can also show electroneurography and alert signals, and can also play audio signals.

Before surgery, sterilizing a patient according to routine procedures, attaching the peripheral electrode 13 to an affected side of the patient and placing a surgical towel; connecting one end of the main wire 2 to the main unit 1 positioned under an operation table, connecting another end of the main wire 2 to the positive electrode branch wire 11; connecting the positive electrode branch wire 11 with the peripheral electrode 13 via the positive electrode branch wire switch 12; the surgery is now started, and when probing an unimportant nerve distribution area, selecting the positive electrode nerve probe 16 for separating and exposing tissues, or separating the positive electrode nerve probe 16 from the positive electrode branch wire electrode insertion end 14, and directly using the positive electrode nerve probe 16 alone for separating and exposing the tissues; according to the practical needs of the surgery, the negative electrode nerve probe 10 can also be operated according to the operation of the positive electrode nerve probe 16; during surgery, when probing an important nerve distribution area or an uncertain area, turning on the main unit 1, setting the intensity and frequency of the output electrical stimulation; if probing for motor nerves in a tissue region, the probing is carried out by unipolar nerve stimulation, specifically, switching the positive electrode branch wire switch 12 to the peripheral electrode 13, and turning on the negative electrode nerve probe switch 6, so that the negative electrode nerve probe 10 and the peripheral electrode 13 form a unipolar electrode stimulation path, and a unipolar stimulation is performed by the negative electrode nerve probe front end conductor 8, or a front end of the negative electrode nerve probe 10 is shaped into a curved shape or a hook shape to perform probing, separating and exposing nerves in tissues of different body parts; after probing, it can be determined whether the tissue contain any motor nerves or mixed nerve distribution, and then a corresponding surgical treatment can follow; if there are muscle reactions due to response of a nerve to electrical stimulation, the intensity of stimulation is adjusted from large to small to preliminarily determine a distance between the nerve and the electrode stimuli; in theory, a distance between the nerve stimulation point and the nerve is linearly related to the intensity of stimulation: the smaller the intensity of the current is, the closer the stimulation point is to the nerve. If probing for a routing of the motor nerves in the tissue region, probing is carried out by bipolar nerve stimulation, specifically, switching the positive electrode branch wire switch 12 to the positive electrode nerve probe 16, and turning on the negative electrode nerve probe switch 6, and the negative electrode nerve probe 10 and the positive electrode nerve probe 16 form a bipolar stimulation path, and the bipolar nerve stimulation is used to probe motor or mixed nerves to discover nerve distribution and routing; after probing, it is known whether the tissue contains motor or mixed nerves distribution, and then a corresponding surgical treatment will be carried out, so as not to damage the nerves during surgery; if after probing, the tissue is found to contain motor or mixed nerves distribution, continue to separate and expose the nerves of the tissue with the help of unipolar or bipolar nerve stimulation, so as not to damage the nerves during surgery; if there is no corresponding muscle reaction or electrophysiological sign in response to the electrical stimulation of the corresponding nerve distribution area, it is determined that the corresponding nerve function is damaged, and then probing and repair treatment of the damaged nerve can be performed timely, thereby improving the safety and quality of the surgery; according to operation requirements of different surgical sites, the positive electrode nerve probe 16 or the negative electrode nerve probe 10 may be disconnected from their respective insertion ends, and being replaced with another positive electrode nerve probe 16 or negative electrode nerve probe 10 of different types, sizes, and functions; after main operation is completed during surgery, unipolar or bipolar nerve electrical stimulation and intraoperative electrophysiological examination can be used to determine whether peripheral nerve function is damaged; if the peripheral nerve is functionally injured, timely probing and repair can be carried out, thereby improving the safety and quality of the operation.

The unipolar electrical stimulation and bipolar electrical stimulation in neuroelectrophysiologic monitoring work as follows: in unipolar electrical stimulation, the current spreads around, and by observing neuromuscular reaction, it can only be determined whether the stimulation point and the adjacent tissue contain motor and/or mixed nerve; in bipolar electrical stimulation, the current flows between the positive and negative electrodes; only existence of motor nerve and/or mixed nerve between the positive and negative electrodes can cause corresponding neuromuscular reaction. Therefore, the bipolar electrical stimulation can better determine routing of the nerves and separate them from the tissue. Specifically, when unipolar electrical stimulation is used, current flows from the stimulating electrode in various directions, and whether or not a reaction occurs depends on a distance between the nerve and a tip of the stimulating electrode, resistance of the tissue therebetween, and the intensity of stimulation; in bipolar electrical stimulation, the current generated by the stimulating electrode only flows from the tip of one stimulating electrode to the tip of the other stimulating electrode, and only the nerves directly positioned along the flowing path of the current between the two stimulating electrodes can be stimulated. Unipolar electrical stimulation is more likely to trigger reaction than bipolar electrical stimulation. Bipolar electrical stimulation is less likely to trigger reaction than unipolar electrical stimulation, because stimulation occurs only when the nerve is between the two electrodes, but bipolar electrical stimulation can more precisely position a boundary of the nerve to guide the surgeon to identify a routing of the nerve than unipolar electrical stimulation. The electrodes of bipolar electrical stimulation can be formed by juxtaposing two unipolar stimulation electrodes. During probing, the unipolar stimulation electrode is used to probe and determine an approximate position of the nerve, and then the bipolar stimulation electrodes are used to accurately delineate the routing of the nerve by observing neural reactions, thereby quickly positioning the nerve, avoiding direct damage to the nerve, shortening the time required for intraoperative diagnosis and also the surgery time, thereby improving the success rate of operation and the quality of life of the patient after surgery.

In clinical anesthesia, a nerve stimulator is used for probing a nerve in an application concerning nerve blocking. When the neurophysiologic monitoring and probing system is used for locating peripheral nerve blocking, the nerve stimulator emits a stimulating current, and the peripheral nerve is pulse-stimulated. If the nerve contains motor fibers, the stimulating current can cause contraction of the muscle innervated by the nerve. The probe of the neurophysiologic monitoring and probing system used in clinical anesthesia is only conductive at the tip, the body of the probe is covered by an insulating material, and the rear part of the probe has a wire connected to the nerve stimulator; the positive electrode of the nerve stimulator is connected through an electrode to the skin of the patient outside a piercing area of the probe, and the negative electrode is connected to the insulated probe, according to this operation, only the unipolar stimulating electrode is used for only getting proximal to the nerve and does not directly contact the nerve to avoid nerve damage; when the tip of the probe pierces through the skin of the patient, set the stimulating current being output to 1 Hz, 1-2 mA/0.1 ms, and the stimulation effect is determined by observing contraction of muscle innervated by the blocked motor nerve. Once reaction occurs, the intensity of current stimulation is gradually reduced. If muscle tremor is still present when the current has a low intensity of 0.3-0.5 mA, it is determined that the probe is positioned the closest to the nerve. The position of the tip of the insulated probe is determined by observing the contraction effect of muscle innervated by suspected blocked nerve at the minimum stimulation current. The smaller the stimulation current is, the closer the tip of the probe is to the nerve.

Use of the multifunctional neurophysiologic monitoring and probing system in neurophysiologic probing during a surgery of internal fixation of bone fracture pertaining to humerus fracture:

1. The patent is subject to routine physical examination before surgery of the humerus fracture, to preliminarily determine whether peripheral nerve injury exists.

2. The patient enters the operating room and is subject to routine anesthesia.

3. In situation where the patient after preoperative physical examination is determined to have no peripheral nerve injury:

(1) sterilizing the patient according to routine procedures, attaching the peripheral electrode 13 to the forearm of the affected side of the patient and placing a surgical towel; lowering the main wire 2 of the sterilized multifunctional neurophysiologic monitoring and probing system from the operation table, and connecting the main wire 2 to the main unit 1 positioned under the operation table, and then connecting the positive electrode branch wire 11 to the peripheral electrode 13.

(2) At the beginning of the operation, when probing an unimportant nerve distribution area, selecting the positive electrode nerve probe 16 for separating and exposing tissues, or separating the positive electrode nerve probe 16 at the positive electrode nerve probe connecting opening 15 from the positive electrode branch wire electrode insertion end 14, and directly using the positive electrode nerve probe 16 for separating and exposing the tissues; according to the practical needs of the surgery, the negative electrode nerve probe 10 can also be operated according to the operation of the positive electrode nerve probe 16.

(3) At the beginning of the operation, when probing an important nerve distribution area or an uncertain area, turning on the main unit 1, setting the intensity and frequency of the output electrical stimulation, wherein the intensity is adjusted from large to small; if probing for motor nerves in a tissue region, the probing is carried out by unipolar nerve stimulation, specifically, switching the positive electrode branch wire switch 12 to the peripheral electrode 13, and turning on the negative electrode nerve probe switch 6, so that the negative electrode nerve probe 10 and the peripheral electrode 13 form a unipolar electrode stimulation path, and a unipolar stimulation is performed by the negative electrode nerve probe front end conductor 8; if there are muscle reactions due to response of a nerve to electrical stimulation, the intensity of stimulation is reduced from large to small to determine a distance between the nerve and the electrode stimuli; or a front end of the negative electrode nerve probe 10 is shaped into a curved shape or a hook shape etc to perform probing, separating and exposing nerves in tissues of different body parts, and it is particularly advantageous for neurophysiologic monitoring and probing and tissue separation in deep tissue and the back thereof; after probing, it is known whether the tissue contains motor or mixed nerves distribution, and then a corresponding surgical treatment will be carried out; if probing for a routing of motor nerves in the tissue region, probing is carried out by bipolar nerve stimulation, specifically, switching the positive electrode branch wire switch 12 to the positive electrode nerve probe 16, and turning on the negative electrode nerve probe switch 6, and the negative electrode nerve probe 10 and the positive electrode nerve probe 16 form a bipolar stimulation path, and the bipolar nerve stimulation is used to probe motor or mixed nerves to discover nerve distribution and routing; if after probing, it is known that the tissue does not contain motor or mixed nerves distribution, then a corresponding surgical treatment will be carried out so as not to damage the nerves during surgery; if after probing, the tissue is found to contain motor or mixed nerves distribution, continue to separate and expose the nerves of the tissue with the help of unipolar or bipolar nerve stimulation, so as not to damage the nerves during surgery; if there is no corresponding muscle reaction or electrophysiological sign in response to the electrical stimulation of the corresponding nerve distribution area, it is determined that the corresponding nerve function is damaged, and then probing and repair treatment of the damaged nerve can be performed timely, thereby improving the safety and quality of the surgery.

(4) At the beginning of the operation, according to operation requirements of different surgical sites, the positive electrode nerve probe 16 or the negative electrode nerve probe 10 may be disconnected at their connecting openings from the corresponding insertion ends, and being replaced with another positive electrode nerve probe 16 or negative electrode nerve probe 10 of different types and functions.

(5) after main operation is completed during surgery, unipolar or bipolar nerve electrical stimulation and/or intraoperative electrophysiological examination can be used to determine whether peripheral nerve function is damaged; if the peripheral nerve is functionally injured, timely probing and repair can be carried out, thereby improving the safety and quality of the operation.

4. In situation where the patient after preoperative physical examination is determined to have peripheral nerve injury:

(1) sterilizing the patient according to routine procedures, attaching peripheral electrodes 13 to a distal end and a proximal end of the affected limb of the patient and placing a surgical towel; lowering the main wire 2 of the sterilized multifunctional neurophysiologic monitoring and probing system from the operation table, and connecting the main wire 2 to the main unit 1 positioned under the operation table, and then connecting the positive electrode branch wire 11 to the peripheral electrode 13 at the distal end.

(2) At the beginning of the operation, when probing an unimportant nerve distribution area at the distal end of the affected limb, selecting the positive electrode nerve probe 16 for separating and exposing tissues, or separating the positive electrode nerve probe 16 at the positive electrode nerve probe connecting opening 15 from the positive electrode branch wire electrode insertion end 14, and directly using the positive electrode nerve probe 16 for separating and exposing the tissues; according to the practical needs of the surgery, the negative electrode nerve probe 10 can also be operated according to the operation of the positive electrode nerve probe 16.

(3) At the beginning of the operation, when probing an important nerve distribution area or an uncertain area, turning on the main unit 1, setting the intensity and frequency of the output electrical stimulation, wherein the intensity is adjusted from large to small; if probing for motor nerves in a tissue region, the probing is carried out by unipolar nerve stimulation, specifically, switching the positive electrode branch wire switch 12 to the peripheral electrode 13, and turning on the negative electrode nerve probe switch 6, so that the negative electrode nerve probe 10 and the peripheral electrode 13 form a unipolar electrode stimulation path, and a unipolar stimulation is performed by the negative electrode nerve probe front end conductor 8; or a front end of the negative electrode nerve probe 10 is shaped into a curved shape or a hook shape etc to perform probing, separating and exposing nerves in tissues of different body parts, and it is particularly advantageous for neurophysiologic monitoring and probing and tissue separation in deep tissue and the back thereof; after probing, it is known whether the tissue contains motor or mixed nerves distribution, and then a corresponding surgical treatment will be carried out; if probing for a routing of motor nerves in the tissue region, probing is carried out by bipolar nerve stimulation, specifically, switching the positive electrode branch wire switch 12 to the positive electrode nerve probe 16, and turning on the negative electrode nerve probe switch 6, and the negative electrode nerve probe 10 and the positive electrode nerve probe 16 form a bipolar stimulation path, and the bipolar nerve stimulation is used to probe motor or mixed nerves to discover nerve distribution and routing; if after probing, it is known that the tissue does not contain motor or mixed nerves distribution, then a corresponding surgical treatment will be carried out so as not to damage the nerves during surgery; if after probing, the tissue is found to contain motor or mixed nerves distribution, continue to separate and expose the nerves of the tissue with the help of unipolar or bipolar nerve stimulation, thereby simply and conveniently expose the nerves of the distal end of the affected limb.

(4) At the beginning of the operation, according to operation requirements of different surgical sites, the positive electrode nerve probe 16 or the negative electrode nerve probe 10 may be disconnected at their connecting openings from the corresponding insertion ends, and being replaced with another positive electrode nerve probe 16 or negative electrode nerve probe 10 of different types and functions.

(5) after main operation is completed during surgery, unipolar or bipolar nerve electrical stimulation and/or intraoperative electrophysiological examination can be used to determine whether there are still other damages to the peripheral nerve function; if the peripheral nerve is functionally injured, timely probing and repair can be carried out, thereby improving the safety and quality of the operation.

The present invention can monitor the intraoperative electrophysiological status in real time during surgery, and can also observe movements of muscles innervated by corresponding motor or mixed nerves by unipolar or bipolar electrical stimulation, to locate the positions and routing of the nerves, thereby simply, safely and effectively probe the nerves and complete nerve probing and exposure of free nerves, also the present invention timely detects the integrity of neurologic functions, shortens the operation time, avoids damage to the nerves and timely detects morphological and functional injury of the nerves; positive electrode nerve probe and negative electrode nerve probe are dismountable and replaceable with other types and models of probes to target probing, separating and exposing nerves of the tissues of different parts of the body; the front end conductors of the probes are slightly protruded from the corresponding insulators, and can be shaped into a curved shape or a hook shape etc, to perform probing, separating and exposing nerves in tissues of different body parts, and it is particularly advantageous for neurophysiologic monitoring and probing and tissue separation in deep tissue and the back thereof. As such, the present invention fully exposes nerves, shortens operation time, reduces intraoperative bleeding and nerve damages; one side of each of the positive and negative nerve probes is insulated, and another side is electrically conductive, and this configuration can reduce erroneous determination due to the impact of electrical stimulation on the nerves of non-targeted tissues, accordingly, errors can be reduced.

A preferred embodiment of the present invention is described above. However, the present invention should not be limited by the above description. Any changes, modifications, substitutions, combinations or simplifications without deviating from the essence and principle of the present invention should be considered alternative configurations having equivalent technical effects, and should fall within the scope of protection of the present invention.

What is claimed is:

1. A multifunctional neurophysiologic monitoring and probing system, comprising a main unit, a main wire, negative electrode neurophysiologic monitoring and probing parts and positive electrode neurophysiologic monitoring and probing parts;

wherein one end of the main wire is connected with the main unit; another end of the main wire is divided into two branch wires connecting with the negative electrode neurophysiologic monitoring and probing parts and the positive electrode neurophysiologic monitoring and probing parts respectively; the two branch wires are a negative electrode branch wire and a positive electrode branch wire respectively;

the negative electrode neurophysiologic monitoring and probing parts comprise a negative electrode branch wire insertion end, a negative electrode nerve probe connecting opening, a negative electrode nerve probe, a negative electrode nerve probe switch, a negative electrode nerve probe insulator, a negative electrode nerve probe front end conductor, and a negative electrode nerve probe conductor; one end of the negative electrode branch wire insertion end is configured to interface with the negative electrode branch wire; the negative electrode nerve probe connecting opening is provided on the negative electrode nerve probe; the negative electrode nerve probe connecting opening is connected with another end of the negative electrode branch wire insertion end; the negative electrode nerve probe switch, the negative electrode nerve probe insulator, the negative electrode nerve probe front end conductor, and the negative electrode nerve probe conductor are all provided on the negative electrode nerve probe; the negative electrode nerve probe switch turns on and off a stimulating current output from the main unit; the negative electrode nerve probe insulator wraps the negative electrode nerve probe conductor; the negative electrode nerve probe front end conductor is provided at a top end of the negative electrode nerve probe conductor and protrudes out of the negative electrode nerve probe insulator;

the positive electrode neurophysiologic monitoring and probing parts comprise a positive electrode branch wire switch, a peripheral electrode, a positive electrode branch wire insertion end, a positive electrode nerve probe connecting opening, a positive electrode nerve probe, a positive electrode nerve probe insulator and a positive electrode nerve probe conductor; the peripheral electrode and one end of the positive electrode branch wire insertion end are configured to interface with the positive electrode branch wire via the positive electrode branch wire switch; the positive electrode nerve probe connecting opening is provided on the positive electrode nerve probe; and the positive electrode nerve probe connecting opening is connected with another end of the positive electrode branch wire insertion end; the positive electrode nerve probe insulator and the positive electrode nerve probe conductor are both provided on the positive electrode nerve probe; the positive electrode nerve probe insulator wraps the positive electrode nerve probe conductor;

the main unit controls an intensity and frequency of electrical stimulation being output, and the main unit also shows electroneurography and alert signals, and also plays audio signals.

2. The multifunctional neurophysiologic monitoring and probing system of claim 1, wherein the negative electrode nerve probe connecting opening is removable from the negative electrode branch wire for replacement of other different negative electrode nerve probes of different types and functions.

3. The multifunctional neurophysiologic monitoring and probing system of claim 1, wherein the positive electrode nerve probe connecting opening is removable from the positive electrode branch wire for replacement of other different positive electrode nerve probes of different types and functions.

4. The multifunctional neurophysiologic monitoring and probing system of claim 1, wherein the negative electrode nerve probe is shapable into an arc shape or a hook shape.

5. The multifunctional neurophysiologic monitoring and probing system of claim 1, wherein the positive electrode nerve probe is shapable into an arc shape or a hook shape.

6. The multifunctional neurophysiologic monitoring and probing system of claim 1, wherein the negative electrode nerve probe insulator of the negative electrode nerve probe only partially wraps the negative electrode nerve probe conductor, wherein one side of the negative electrode nerve probe is insulated, and another side of the negative electrode nerve probe remains electrically conductive.

7. The multifunctional neurophysiologic monitoring and probing system of claim 1, wherein the positive electrode nerve probe insulator of the positive electrode nerve probe only partially wraps the positive electrode nerve probe conductor, wherein one side of the positive electrode nerve probe is insulated, and another side of the positive electrode nerve probe remains electrically conductive.

8. A method of implementing the multifunctional neurophysiologic monitoring and probing system according to claim 1, comprising the following steps:
  (1) before surgery starts, sterilizing a patient according to routine procedures, attaching the peripheral electrode to an affected side of the patient, and placing a surgical towel; connecting one end of the main wire to the main unit positioned under an operation table, and connecting another end of the main wire with the positive electrode branch wire, and then connecting the positive electrode branch wire with the peripheral electrode via the positive electrode branch wire switch;
  (2) starting the surgery; when probing an unimportant nerve distribution area, selecting the positive electrode nerve probe for separating and exposing tissues, or separating the positive electrode nerve probe from the positive electrode branch wire insertion end, and directly using the positive electrode nerve probe alone for separating and exposing the tissues; according to practical needs of the surgery, processing the negative electrode nerve probe in the same way as the positive electrode nerve probe;
  (3) during the surgery, when probing an important nerve distribution area or an uncertain area, turning on the main unit, setting an intensity and frequency of the electrical stimulation being output; when probing for a motor nerve in a tissue region, performing the probing by unipolar nerve stimulation, which comprises switching the positive electrode branch wire switch to the peripheral electrode, and turning on the negative electrode nerve probe switch to form a unipolar nerve stimulation path using the negative electrode nerve probe and the peripheral electrode, and performing the unipolar nerve stimulation via the negative electrode nerve probe front end conductor; alternatively, shaping a front end of the negative electrode nerve probe into a curved shape or a hook shape to perform probing, separating and exposing nerves in tissues of different body parts; after probing, determining whether the tissue contains any motor or mixed nerve distribution, and then carrying out a corresponding surgical treatment; when there are muscle reactions due to response of the nerve to the electrical stimulation, reducing the intensity of the electrical stimulation from large to small, to preliminarily determine a distance between the nerve and a corresponding electrode stimuli; when probing for a routing of the motor nerve in the tissue region, performing the probing by bipolar nerve stimulation, which comprises switching the positive electrode branch wire switch to the positive electrode nerve probe, and turning on the negative electrode nerve probe switch to form a bipolar nerve stimulation path using the negative electrode nerve probe and the positive electrode nerve probe, and performing the bipolar nerve stimulation to probe the motor or mixed nerve to discover nerve distribution and routing; after probing, determining whether the tissue contain any motor or mixed nerve distribution, and then carrying out a corresponding surgical treatment to prevent the surgery from damaging the nerve; wherein,
  when the tissue is found to contain motor or mixed nerve distribution after probing, continuing to separate and expose the nerve of the tissue by using the unipolar nerve stimulation or the bipolar nerve stimulation, so as not to damage the nerve during surgery; when there is no corresponding muscle reaction or electrophysiological sign in response to the electrical stimulation of a corresponding nerve distribution area, confirming a corresponding damage of nerve function, and then timely performing probing and repair treatment of the damaged nerve, thereby improving safety and quality of the surgery;
  (4) after major operation is completed during the surgery, determining whether peripheral nerve is functionally damaged using the unipolar nerve stimulation or the bipolar nerve stimulation and/or intraoperative electrophysiological examination, and if yes, timely performing probing and repair of damaged peripheral nerve, thereby improving safety and quality of the operation.

9. The method of implementing the multifunctional neurophysiologic monitoring and probing system of claim 8, wherein, according to operation requirements of different surgical sites, disconnecting the positive electrode nerve probe or the negative electrode nerve probe from their corresponding insertion ends, and replacing the positive electrode nerve probe or the negative electrode nerve probe with another positive electrode nerve probe or another negative electrode nerve probe of different types and functions respectively.

* * * * *